US007364295B2

United States Patent
Tawada (10) Patent No.: US 7,364,295 B2
(45) Date of Patent: Apr. 29, 2008

(54) FUNDUS CAMERA

(75) Inventor: Akira Tawada, Gamagori (JP)

(73) Assignee: Nidek Co., Ltd., Gamagori (JP)

( * ) Notice: Subject to any disclaimer, the term of this patent is extended or adjusted under 35 U.S.C. 154(b) by 136 days.

(21) Appl. No.: 11/289,431

(22) Filed: Nov. 30, 2005

(65) Prior Publication Data

US 2006/0114412 A1 Jun. 1, 2006

(30) Foreign Application Priority Data

Dec. 1, 2004 (JP) .............................. 2004-349033

(51) Int. Cl.
*F16K 3/32* (2006.01)
*F16K 1/14* (2006.01)

(52) U.S. Cl. ...................................... 351/205; 351/211
(58) Field of Classification Search .................. 351/206
See application file for complete search history.

(56) References Cited

U.S. PATENT DOCUMENTS 5,463,430 A    10/1995   Isogai et al.
6,669,339 B2 *  12/2003  Nanjyo ....................... 351/206
2005/0068496 A1 *  3/2005  Ichikawa ................... 351/206
2005/0117115 A1    6/2005  Ichikawa

FOREIGN PATENT DOCUMENTS

| JP | A-06-046999 | 2/1994 |
| JP | A-08-275921 | 10/1996 |
| JP | 2000-005131 | 1/2000 |

* cited by examiner

*Primary Examiner*—Jordan Schwartz
*Assistant Examiner*—James C Jones
(74) *Attorney, Agent, or Firm*—Oliff & Berridge, PLC (57) ABSTRACT

A fundus camera, of which usability is enhanced while offering an excellent combination of automatic and manual photographing, includes a photographing optical system having a photographing optical axis, a movable focusing lens and an image-pickup element, alignment-state detection means, focusing-state detection means, a fixation target presenting unit where a presenting position of a fixation target is changeable between a reference position for photographing a central portion and a peripheral position for photographing a peripheral portion, a photographing starting switch, means for switching between a manual mode in which photographing is performed based on a signal from the switch and an automatic mode in which photographing is automatically performed.

8 Claims, 6 Drawing Sheets

FUNDUS CAMERA

BACKGROUND OF THE INVENTION

1. Field of the Invention

The present invention relates to a fundus camera for photographing a fundus of an eye to be examined.

2. Description of Related Art

Conventionally, proposed is a fundus camera which has an automatic alignment function of automatically aligning a photographing optical system with an eye to be examined, an automatic focusing function of automatically focusing the photographing optical system on a fundus of the eye, and an automatic photographing function of automatically photographing the fundus based on detection results on an alignment state and a focus state (e.g., Japanese Patent Application Unexamined Publication No. Hei8-275921).

In such a fundus camera, a central portion of the fundus can be photographed relatively favorably in automatic mode (i.e., a mode of automatic alignment, automatic focusing and automatic photographing); however, in the case of photographing a peripheral portion of the fundus, it is difficult to perform the automatic alignment and the automatic focusing since a photographing optical axis deviates significantly from a visual axis of the eye, causing difficulties in the automatic photographing. Hence, when photographing a peripheral portion of the fundus, it is frequently more preferable to switch to manual mode of performing manual photographing with a photographing starting switch after performing manual alignment and focusing.

However, in the case of photographing the central portion of the fundus after photographing the peripheral portion of the fundus in the manual mode and switching to the automatic mode, a lot of trouble is given since there emerge needs both for operation of switching from the manual mode to the automatic mode, and operation of changing a presenting position of a fixation target from a position for photographing the peripheral portion of the fundus to a position for photographing the central portion of the fundus. In addition, also in the case of photographing the peripheral portion of the fundus after photographing the central portion of the fundus in the automatic mode and switching to the manual mode, a lot of trouble is given since there emerge needs both for operation of switching from the automatic mode to the manual mode, and operation of changing the presenting position of the fixation target from the position for photographing the central portion of the fundus to the position for photographing the peripheral portion of the fundus.

SUMMARY OF THE INVENTION

An object of the invention is to overcome the problems described above and to provide a fundus camera of which usability is enhanced while offering an excellent combination of automatic photographing and manual photographing.

To achieve the objects and in accordance with the purpose of the present invention, a fundus camera for photographing a fundus of an eye to be examined is provided with a photographing optical system having a photographing optical axis, a focusing lens movable in a direction of the photographing optical axis and an image-pickup element, alignment-state detection means for detecting a state of alignment of the photographing optical system with the eye, focusing-state detection means for detecting a state of focusing of the photographing optical system on the fundus, a fixation target presenting unit which presents a fixation target for guiding a visual line to the eye in which a presenting position of the fixation target is changeable between a reference position which is a position for photographing a central portion of the fundus and a peripheral position which is a position for photographing a peripheral portion of the fundus, a photographing starting switch, photographing-mode switching means for switching between a manual photographing mode in which photographing is performed based on an operation signal from the photographing starting switch and an automatic photographing mode in which photographing is automatically performed based on results detected by the alignment-state detection means and the focusing-state detection means, and fixation target presentation control means for controlling the fixation target presenting unit so that the presenting position of the fixation target is brought to the reference position at the time of switching from the manual photographing mode to the automatic photographing mode even though the presenting position of the fixation target is set to the peripheral position.

In another aspect of the invention, a fundus camera for photographing a fundus of an eye to be examined is provided with a photographing optical system having a photographing optical axis, a focusing lens movable in a direction of the photographing optical axis and an image-pickup element, alignment-state detection means for detecting a state of alignment of the photographing optical system with the eye, focusing-state detection means for detecting a state of focusing of the photographing optical system on the fundus, a fixation target presenting unit which presents a fixation target for guiding a visual line to the eye in which a presenting position of the fixation target is changeable between a reference position which is a position for photographing a central portion of the fundus and a peripheral position which is a position for photographing a peripheral portion of the fundus, a photographing starting switch, photographing-mode switching means for switching between a manual photographing mode in which photographing is performed based on an operation signal from the photographing starting switch and an automatic photographing mode in which photographing is automatically performed based on results detected by the alignment-state detection means and the focusing-state detection means, and presenting-position changing means for inputting a change signal for changing the presenting position of the fixation target, wherein the photographing-mode switching means switches from the automatic photographing mode to the manual photographing mode based on a change signal for changing the presenting position of the fixation target from the reference position to the peripheral position.

Additional objects and advantages of the invention are set forth in the description which follows, are obvious from the description, or may be learned by practicing the invention. The objects and advantages of the invention may be realized and attained by the fundus camera in the claims.

BRIEF DESCRIPTION OF TEE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
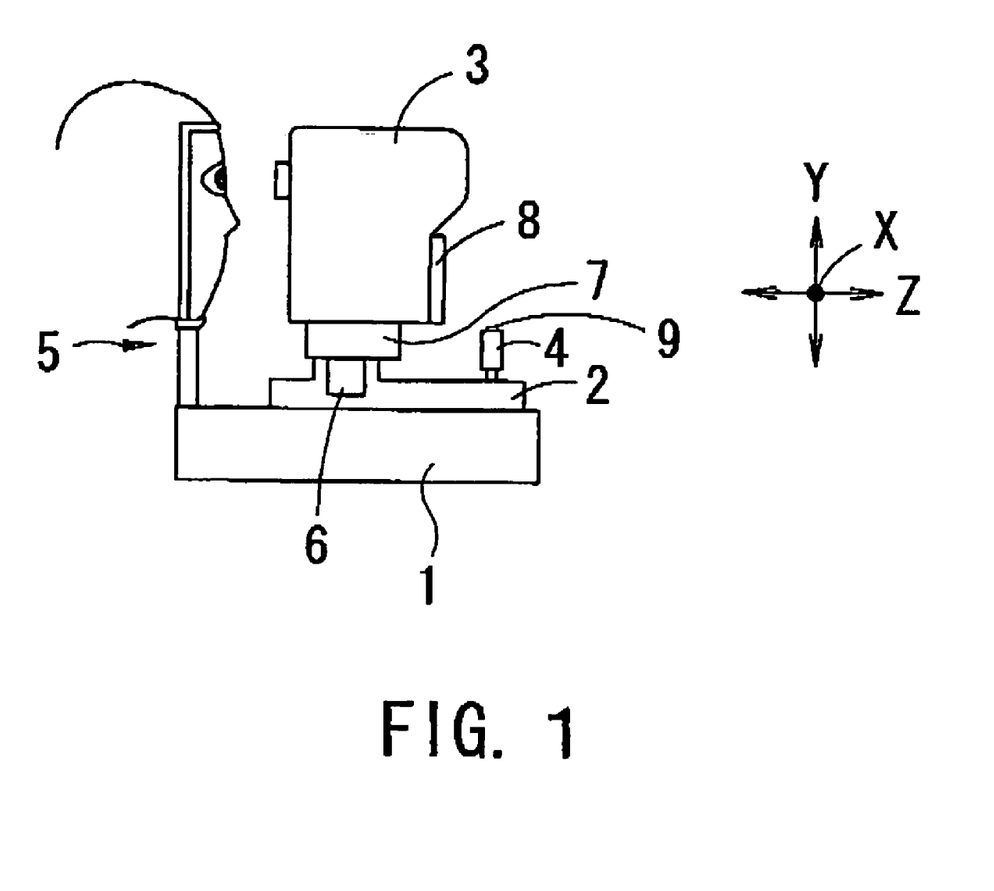
FIG. 1 is a view showing a schematic configuration of a fundus camera of non-mydriasis type consistent with one embodiment of the present invention.

A detailed description of one preferred embodiment of a fundus camera embodied by the present invention is provided below with reference to the accompanying, drawings. FIG. 1 is a view showing a schematic configuration of a fundus camera of non-mydriasis type consistent with the preferred embodiment of the present invention.

The fundus camera is provided with a base 1, a moving base 2 movable in aright-and-left direction (hereinafter referred to as an "X-direction") and a back-and-forth direction (hereinafter referred to as a "Z-direction") with reference to the base 1 by tilting operation of a joystick 4, a photographing unit 3 movable in the right-and-left direction, an up-and-down direction (hereinafter referred to as a "Y-direction"), and the back-and-forth direction with reference to the moving base 2 under control of a control unit 100 to be described later, and a face supporting unit 5 fixedly arranged on the base 1 for supporting a face (head) of an examinee. In an X- and Z-moving unit 7, a Z table movable in the Z-direction is arranged on a Y table, an X table movable in the X-direction is arranged on the Z table, and the photographing unit 3 is arranged on the X table. The X- and Z-moving unit 7 moves the Z and x tables by their respective moving mechanisms consisting of a motor and the like to move the photographing unit 3 in the X- and Z-directions. A Y-moving unit 6 moves the Y table by its moving mechanism consisting of a motor and the like to move the photographing unit 3 in the Y-direction. Besides, for this kind of three-dimensional moving mechanism, a known mechanism may be employed. Further, the photographing unit 3 is moved in the Y-direction also by actuating the Y-moving unit 6 through rotary operation of the joystick 4. A monitor 8 for displaying an observation image and a photographed image is provided on an examiner's part of the photographing unit 3. In addition, on the top part of the joystick 4, provided is a photographing starting switch 9 for implementing manually-operated photographing.

Figure 2:
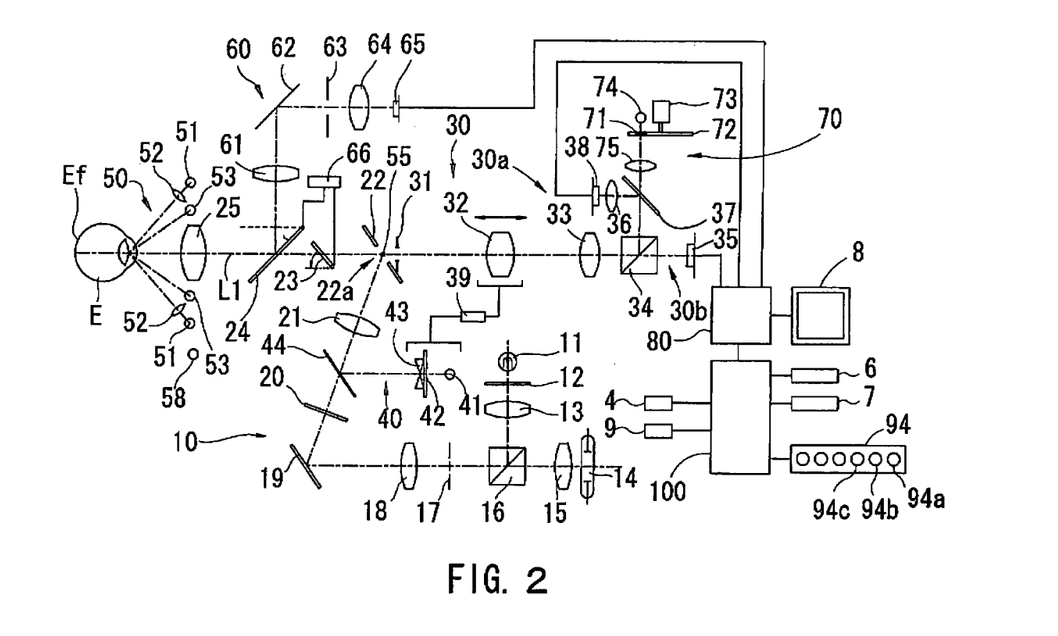
FIG. 2 is a view showing a schematic configuration of an optical system and a control system of the fundus camera.

FIG. 2 is a view showing a schematic configuration of an optical system and a control system housed in the photographing unit 3. The optical system consists of an illumination optical system 10, a fundus observation/photographing optical system 30, a focus target projection optical system 40, an alignment target projection optical system 50, an anterior-segment observation optical system 60 and a fixation target presenting optical system 70.

<Illumination Optical System 10>

The illumination optical system 10 includes an illumination optical system for fundus observation and an illumination optical system for photographing. Illumination light emitted from an illumination light source 11 for fundus observation such as a halogen light is made into infrared illumination light by an infrared transmission filter 12 which transmits light within an infrared wavelength range of approximately 750 nm to approximately 880 nm, and reflected by a dichroic mirror 16 via a condenser lens 13. The dichroic mirror 16 has a wavelength-selecting property of reflecting approximately all light within an infrared wavelength range and transmitting approximately all light within a visible wavelength range. The infrared illumination light reflected by the dichroic mirror 16 passes through a ring-slit plate 17, a relay lens 18, a total reflection mirror 19, a black dot plate 20 having a black dot at its center, a half mirror 44 and a relay lens 21, and is reflected by an apertured mirror 22 to be projected onto a fundus Ef of an eye E of the examinee via an objective lens 25. Besides, an infrared light source such as an infrared light-emitting diode may be used instead of the light source 11 such as a halogen light and the infrared transmission filter 12.

Visible illumination light emitted from a visible illumination light source 14 for photographing such as a flash light passes through a condenser lens 15 and is transmitted through the dichroic mirror 16 to be projected onto the fundus Ef via the ring-slit plate 17 to the objective lens 25.

<Fundus Observation/Photographing Optical System 30>

The fundus observation/photographing optical system 30 includes a fundus observation optical system 30a and a photographing optical system 30b. Infrared reflection light and visible reflection light from the fundus Ef pass through the objective lens 25, an opening (aperture) 22a of the apertured mirror 22, a photographing diaphragm 31 arranged in the vicinity of the opening 22a, a focusing lens 32 and an image forming lens 33 to enter a dichroic mirror 34. The photographing diaphragm 31 is arranged in a position approximately conjugate with a pupil of the eye E with reference to the objective lens 25. The focusing lens 32 is arranged movable by a moving mechanism 39 consisting of a motor and the like in a direction of an optical axis L1 of the fundus observation/photographing optical system 30 (i.e., an optical axis of the objective lens 25). The dichroic mirror 34 has a wavelength-selecting property of reflecting approximately all light within the infrared wavelength range, and reflecting a part (a small proportion) of light within the visible wavelength range and transmitting the other part (a large proportion). The visible reflection light transmitted through the dichroic mirror 34 is photo-received on a CCD camera 35 for photographing having sensitivity to the visible wavelength range to form an image of the fundus Ef. In addition, the infrared reflection light reflected by the dichroic mirror 34 is reflected by a dichroic mirror 37, and photo-received on a CCD camera 38 for fundus observation having sensitivity to the infrared wavelength range via a relay lens 36 to form an image of the fundus Ef. The dichroic mirror 37 has a wavelength-selecting property of reflecting approximately all light within the infrared wavelength range, and transmitting approximately all light within the visible wavelength range. In addition, the CCD camera 38, which doubles as image-pickup means for focus target detection to be described later (i.e., the fundus observation optical system 30a doubles as a focus target detection optical system), picks up the image of the fundus Ef formed by the light source 11 and images of the focus targets formed by the focus target projection optical system 40 to be described later. Besides, it is advantageous to make fundus photographing means double as focus target projection means as in the present embodiment; however, focus target projection means intended only for the purpose may be provided separately.

On an optical path between the objective lens 25 and the apertured mirror 22 (the diaphragm 31), a movable dichroic mirror 24 is arranged as an optical path dividing member. Further, on an optical path between the dichroic mirror 24 and the apertured mirror 22 (the diaphragm 31), a movable parallel glass plate 23 is arranged as a member for correcting a deviation of an optical axis caused by the dichroic mirror 24. The dichroic mirror 24 has a wavelength-selecting property of reflecting approximately all light within an infrared wavelength range of approximately 900 nm or more including light from an infrared illumination light source 58 for anterior-segment observation to be described later and that from the alignment target projection optical system 50 to be described later, and transmitting approximately all light within an infrared wavelength range of approximately 900 nm or less including light from the illumination optical system for fundus observation and that from the focus target projection optical system 40 to be described later. At the time of photographing, the dichroic mirror 24 and the glass plate 23 are flipped up synchronously by an inserting and removing mechanism 66 to be removed from the optical path. Besides, a known mechanism such as a solenoid and cam (or motor and the like) can be used for the inserting and removing mechanism 66.

<Focus Target Projection Optical System 40>

Infrared target light emitted from an infrared light source 41 such as an infrared light-emitting diode which emits infrared light having a center wavelength of approximately 880 nm, passes through a slit target plate 42 and two deflection-angle prisms 43 attached to the target plate 42, and is reflected by the half mirror 44, and further passes through the relay lens 21 to the objective lens 25 to be projected onto the fundus Ef (i.e., the focus targets are projected thereonto). The light source 41 and the target plate 42 are moved in synchronization with the focusing lens 32 in the optical axis direction by the moving mechanism 39.

<Alignment Target Projection Optical System 50>

The alignment target projection optical system 50 includes two first projection optical systems in a pair which have optical axes arranged symmetrically with respect to the optical axis L1, and two second projection optical systems in a pair which have optical axes arranged symmetrically with respect to the optical axis L1 at an angle narrower than that of the optical axes of the first projection optical systems. The first projection optical systems in a pair include infrared light sources 51 such as an infrared light-emitting diode which emits infrared light having a center wavelength of approximately 940 nm, and collimating lenses 52 respectively, and project infrared target light at an infinite distance onto the eye E with approximately parallel light (i.e., project alignment targets). On the other hand, the second projection optical systems in a pair include infrared light sources 53 such as an infrared light-emitting diode which emits infrared light having a center wavelength of approximately 940 nm, and project infrared target light at a finite distance onto the eye E with divergent light (i.e., project alignment targets). Besides, in FIG. 2 which is a side view showing the optical system, the alignment target projection optical system 50 is illustrated as arranged in an up-and-down direction; however it is actually arranged in a right-and-left direction.

In addition, on the periphery of the opening 22a of the apertured mirror 22, two infrared light sources 55 which emit infrared light having a center wavelength of approximately 880 nm in order to form working dots are arranged symmetrically with respect the optical axis L1. The light sources 55 are arranged in a manner that their conjugate position is at a distance corresponding to a half of a corneal radius of curvature of the eye E when a working distance between the eye E and the objective lens 25 becomes proper.

<Anterior-Segment Observation Optical System 60>

Infrared illumination light emitted from the illumination light source 58 for anterior-segment observation such as an infrared light-emitting diode which emits infrared light having a center wavelength of approximately 940 nm is reflected by an anterior-segment of the eye E and the dichroic mirror 24, and passes through a field lens 61, a total reflection mirror 62, a diaphragm 63 and a relay lens 64, and is photo-received on a CCD camera 65 for anterior-segment observation having sensitivity to the infrared wavelength range to form an image of the anterior-segment of the eye E. In addition, the CCD camera 65, which doubles as image-pickup means for alignment target detection (i.e., the anterior-segment observation optical system 60 doubles as an alignment target detection optical system), picks up the image of the anterior-segment of the eye E formed by the light source 58 and images of the alignment targets formed by the alignment target projection optical system 50. Besides, it is advantageous to make anterior-segment-image pickup means double as alignment target detection means as in the present embodiment; however, alignment target detection means intended only for the purpose may be provided separately.

<Fixation Target Presenting Optical System 70>

Figure 4:
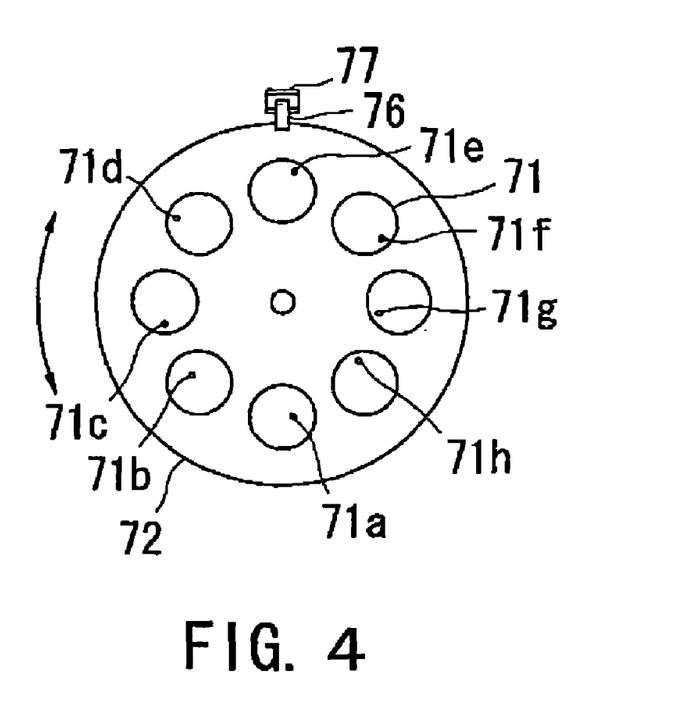
FIG. 4 is a view showing a schematic configuration of a rotary disk in a fixation target presenting optical system.
Figure 5A:
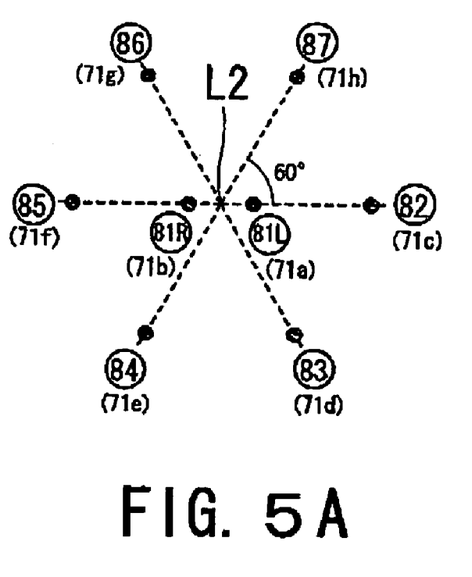
FIGS. 5A and 5B are views showing presenting positions of a fixation target and their corresponding regions on a fundus to be photographed.

Red fixation target light emitted from a fixation target light source (fixation lamp) 74 such as a red light-emitting diode passes through an opening (aperture) in a shielding plate 71 of a rotary disk 72 and a relay lens 75 to be transmitted through the dichroic mirror 37. A part of the red fixation target light transmitted through the dichroic mirror 37 is reflected by the dichroic mirror 34 to be projected onto the fundus Ef via the image forming lens 33 to the objective lens 25 (i.e., a fixation target is projected onto the fundus Ef). As shown in FIG. 4, the disk 72 includes the eight shielding plates 71 which are respectively provided with openings (apertures) 71a-71h. The disk 72 is rotated by a pulse motor 73, and one of the eight shielding plates 71 is selectively arranged in front of the light source 74. As shown in FIG. 5A, such a selective arrangement of the shielding plates 71 allows a fixation target to be presented in eight positions 81L, 81R and 82-87 corresponding to the eight openings 71a-71h with respect to an optical axis L2 of the fixation target presenting optical system 70 (i.e., an optical axis of the relay lens 75). Besides, the optical axis L2 is made coaxial (or, made to have a predetermined positional relationship) with the optical axis L1. An initial position for rotation of the disk 72 is detected through a shielding plate 76 and a sensor 77 provided with a photo-projecting/receiving part, The control unit 100 controls a rotation angle by the pulse motor 73 so that each of the openings 71a-71h may be arranged in front of the light source 74.

Figure 5B:
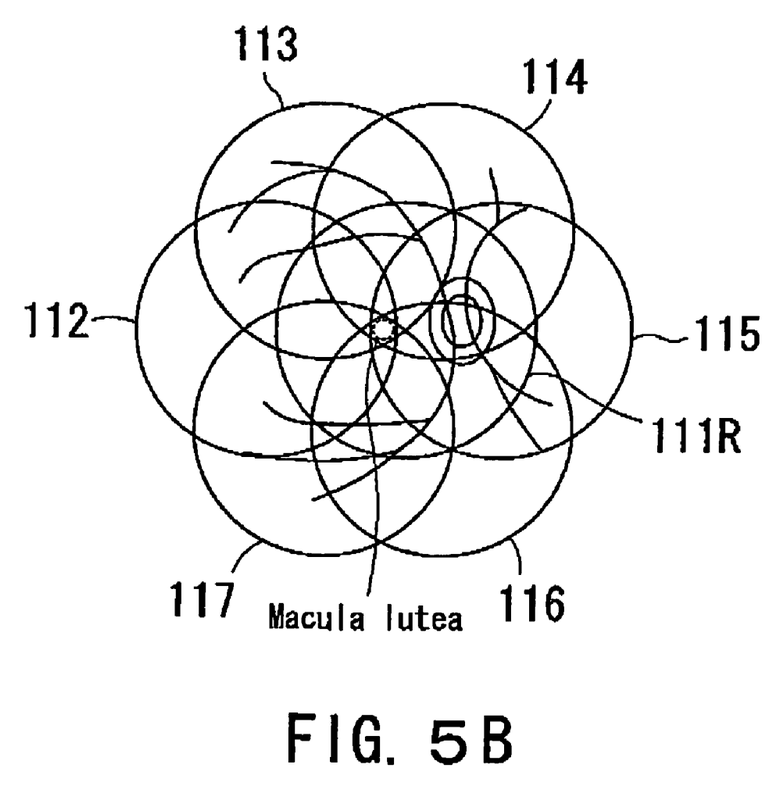

Incidentally, the position 81L corresponding to the opening 71a is a fixation target presenting position used at the time of photographing a central portion of a fundus of a left eye which has its center in the vicinity of a posterior pole including a macula lutea and an optic papilla, and is defined as a reference position at the time of photographing the fundus of the left eye. The position 81R corresponding to the opening 71b is a fixation target presenting position used at the time of photographing a central portion of a fundus of a right eye which has its center in the vicinity of a posterior pole, and is defined as a reference position at the time of photographing the fundus of the right eye. The positions 82-87 corresponding to the openings 71c-71h are fixation target presenting positions used at the time of photographing peripheral portions of the fundi of the right and left eyes (i.e., peripheral positions). FIG. 5B is a view illustrating regions on the fundus to be photographed when the fixation target is presented respectively in the positions 81R and 82-87 at the time of photographing the fundus of the right eye, where the regions 111R and 112-117 are corresponding respectively to the positions 81R and 82-87. Besides, as the fixation target presenting positions for photographing the peripheral portion of the fundus, selected is a position which allows a fundus image desired depending on conditions such as diabetic retinopathy and glaucoma to be photographed.

Figure 3:
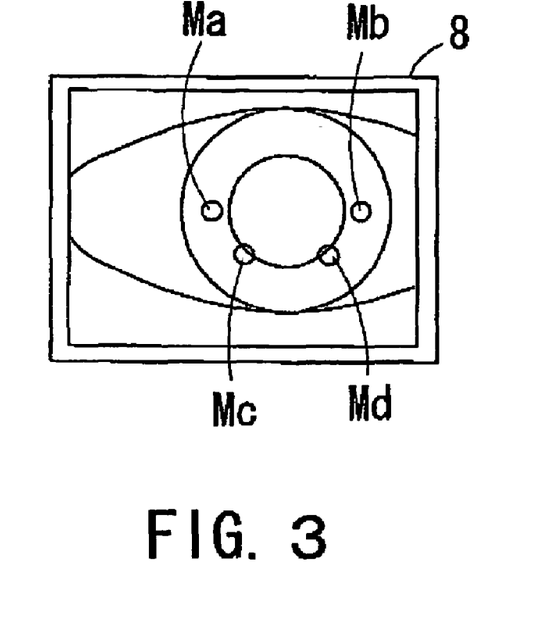
FIG. 3 is a view showing an example of an observation image of an anterior-segment of an eye displayed on a monitor.

At the time of anterior-segment observation and alignment, the dichroic mirror 24 and the glass plate 23 are inserted in the optical path of the fundus observation/photographing optical system 30 (the optical path between the objective lens 25 and the apertured mirror 22). The anterior-segment image formed by the light source 58 and the alignment target images formed by the alignment target projection optical system 50 are reflected by the dichroic mirror 24 and picked up by the CCD camera 65. FIG. 3 is a view shoving the anterior-segment image and the alignment target images which are picked up by the CCD camera 65 and displayed on the monitor 8. Target images Ma and Mb are the alignment target images at an infinite distance formed by the first projection optical system, and target images Mc and Md are the alignment target images at a finite distance formed by the second projection optical system.

Figure 6:
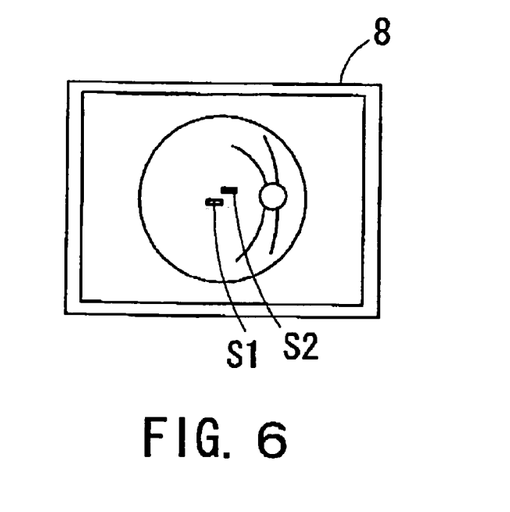
FIG. 6 is a view showing an example of an observation image of the fundus displayed on the monitor.

Also at the time of fundus observation and focusing, the dichroic mirror 24 and the glass plate 23 are inserted in the optical path of the fundus observation/photographing optical system 30. An image of the fundus formed by the illumination optical system for fundus observation and images of the focus targets formed by the focus target projection optical system 40 are transmitted through the dichroic mirror 24 and the glass plate 23 and picked up by the CCD camera 38. FIG. 6 is a view showing the fundus image and the focus target images which are picked up by the CCD camera 38 and displayed on the monitor 8. Target images S1 and S2 are the focus target images formed by the focus target projection optical system 40.

On the other hand, at the time of photographing, the dichroic mirror 24 and the glass plate 23 are removed from the optical path of the fundus observation/photographing optical system 30 by the inserting and removing mechanism 66, and the image of the fundus Ef is picked up by the CCD camera 35 via the objective lens 25 to the dichroic mirror 34. Besides, a configuration such that a camera for photographing doubles as a camera for fundus observation is also available.

Respective image signals outputted from the CCD cameras 65, 38 and 35 are inputted to an image processing unit 80. The image processing unit 80 detects the alignment target images based on the image signal from the CCD camera 65 and the focus target images based on the image signal from the CCD camera 38. In addition, the image processing unit 80 is connected to the monitor 8 to control an image to be displayed thereon. The control unit 100 is connected with the image processing unit 80, the Y-moving unit 6, the X- and Z-moving unit 7, the joystick 4, the moving mechanism 39, the inserting and removing mechanism 66, the pulse motor 73, a photographing starting switch 9, a switch part 94 having various switches, the light sources, and the like. (In FIG. 2, a part of connection lines is not illustrated.)

In the switch part 94, a switch 94a is for switching (selecting) between a manual photographing mode in which the examiner performs alignment and focusing through operation of the joystick 4 as well as photographing through operation of the photographing starting switch 9, and an automatic photographing mode in which the control unit 100 drives and controls the X- and Z-moving unit 7 and the Y-moving unit 6 to perform alignment and focusing based on information respectively on an alignment state and a focusing state detected by the image processing unit 80, and photographing is automatically performed when the alignment state and the focusing state meet their respective completion conditions. A switch 94b, which is for changing a presenting position of the fixation target, can selectively change the presenting position to either of the positions 81L, 81R and 82-87. A switch 94c is a switch (dial) for performing manual focusing.

Hereinafter, an operation of the apparatus having the above-described configuration will be described. Here, a case will be described where the central portion of the fundus of the right eye is photographed and the peripheral portion of the same is subsequently photographed.

In the case of photographing the central portion of the fundus, it is more convenient to use the automatic photographing mode in order to facilitate work in photographing. Accordingly, the automatic photographing mode is selected first using the switch 94a, and the position 81R for photographing the central portion of the fundus of the right eye is selected using the switch 94c.

Next, the examinee's face is supported by the face supporting unit 5. Then, the examinee is instructed to fixate the fixation target. In the early stage of the alignment, the dichroic mirror 24 and the glass plate 23 are inserted in the optical path of the fundus observation/photographing optical system 30, and the anterior-segment image picked up by the CCD camera 65 is displayed on the monitor 8. While observing the anterior-segment image displayed on the monitor 8, the examiner moves the photographing unit 3 in the X- and Y-directions so that the anterior-segment image is positioned at the center of a screen of the monitor 8, and further moves the photographing unit 3 in the Z-direction so that the anterior-segment image comes into focus. When the anterior-segment image is positioned at the center of the screen of the monitor 8, the four target images Ma, Nb, Mc and Md are also displayed (reflected) there as shown in FIG. 3 to be detected by the image processing unit 80. Based on the detected target images Ma-Md, the control unit 100 obtains the information on the alignment state in the X-, Y- and Z-directions. In other words, the control unit 100, regarding the intermediate position between the target images Ma and Mb as a corneal vertex position, obtains an amount of deviation (positional displacement) from a reference position for alignment in the X- and Y-directions. Based on this information, the control unit 100 drives and controls the X- and Z-moving unit 7 and the Y-moving unit 6 to perform alignment of the photographing unit 3 in the X- and Y-directions. Further, the control unit 100 obtains an amount of deviation (positional displacement) from a reference position for alignment in the Z-direction by comparing an interval between the target images Ma and Mb formed by the infinite light sources and an interval between the target images Mc and Md formed by the finite light sources. Then, based on this information, the control unit 100 drives and controls the X- and Z-moving unit 7 to perform alignment of the photographing unit 3 in the Z-direction (for more details, refer to U.S. Pat. No. 5,463,430 (Japanese Patent Application Unexamined Publication No. Hei6-46999)).

When the alignment in the X-, Y- and Z-directions comes into completion, the two target images S1 and S2 are detected by the image processing unit 80. Based on separation information on the detected target images S1 and S2, the control unit 100 performs focusing on the fundus Ef by driving and controlling the moving mechanism 39 to move the light source 41, the target plate 42 and the focusing lens 32 in the optical axis direction so that the target images S1 and S2 coincide with each other.

When completion of the alignment in the X-, Y- and Z-directions and completion of the focusing are detected, the control unit 100 controls a display on the monitor 8 to be switched from the anterior-segment image to the fundus image. Further, once the automatic focusing is completed, the control unit 100 controls to stop (prohibit) the actuation of the automatic focusing until a signal for instructing the actuation of the automatic focusing is provided (inputted).

Then, when a predetermined time elapses after the display on the monitor 8 is switched to the fundus image, the control unit 100 controls to perform photographing of the fundus automatically. The control unit 100 drives and controls the inserting and removing mechanism 66 to remove the dichroic mirror 24 and the glass plate 23 from the optical path and make the light source 14 emit light. By the emission of the light from the light source 14, the fundus Ef is illuminated with the visible light, and reflection light from the fundus Ef is photo-received on the CCD camera 35 to form an image of the fundus Ef. On the monitor 8, the fundus image picked up by the CCD camera 35 is displayed in color. Further, the fundus image (photographed image) is stored in an image memory included in the image processing unit 80.

Figure 7A:
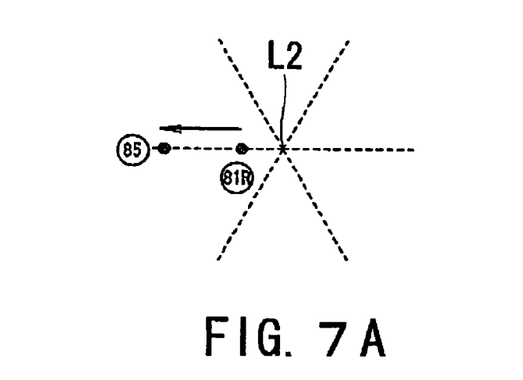
FIGS. 7A and 7B are views showing a change of the presenting position of the fixation target at the time of shifting from photographing of a central portion of the fundus to photographing of a peripheral portion of the fundus, and regions to be photographed which correspond respectively to the presenting positions before and after the shifting.
Figure 7B:
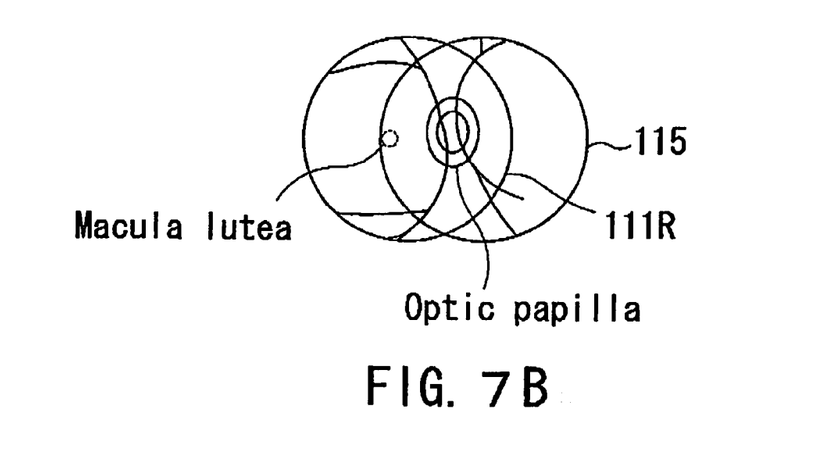

Upon completion of the photographing of the central portion of the fundus, photographing is shifted to that of the peripheral portion of the fundus. In the case of photographing the peripheral portion of the fundus, any one of the positions 82-87 for photographing the peripheral portion of the fundus is selected using the switch 94b. For example, the position 85 is selected in order to photograph a peripheral region 115 including an optic papilla of the right eye. The control unit 100 drives and controls the pulse motor 73 to automatically arrange the shielding plate 71 having the opening 71f in front of the light source 74. Accordingly, the presenting position of the fixation target is brought to the position 85 (see FIG. 7A) to guide a visual axis of the eye E in the direction of the position 85, so that the region 115 (see FIG. 7B) is made ready for observation and photographing. Although there may be a case where an eye position inclines and the target images S1 and S2 chip or blur, a malfunction of the automatic focusing caused by improper detection of the target images S1 and S2 is prevented, since the actuation of the automatic focusing remains to be stopped once the automatic focusing is completed.

In addition, when a signal to change the fixation target position for photographing the central portion of the fundus to the one for photographing the peripheral portion of the fundus is inputted by the switch 94b as described above, the control unit 100 automatically controls to switch from the automatic photographing mode to the manual photographing mode. The mode is switched to the manual photographing mode at the time of photographing the peripheral portion of the fundus because a photographing optical axis deviates significantly from the visual axis of the eye E so that the target images S1 and S2 chip or blur, causing difficulties in automatic focusing, and because a flare and the like which make detection of the alignment target images harder tend to emerge under the same condition as the central portion, causing difficulties in automatic alignment.

When the mode is switched to the manual photographing mode, the examiner observes the fundus image displayed on the monitor 8 to perform fine-adjustment of alignment through operation of the joystick 4 or the like so that an image free from a flare may be observed. In addition, fine-adjustment of focusing is performed by moving the focusing lens 32 through operation of the switch 94c. When a desired portion of the fundus Ef becomes favorably observable, the switch 9 is pushed to perform photographing.

As mentioned above, the automatic photographing mode is switched to the manual photographing mode in synchronization with the change from the fixation target position for photographing the central portion of the fundus to the fixation target position for photographing the peripheral portion of the fundus by the switch 94b, thereby saving the trouble of switch operation.

Next, in the case of photographing a central portion of a fundus in the automatic photographing mode again as an eye to be photographed is switched or another examinee is photographed, when a signal to switch from the manual photographing mode to the automatic photographing mode is inputted by the switch 94a, the control unit 100 controls to change the fixation target position from the one for photographing the peripheral portion of the fundus to the one for photographing the central portion of the fundus.

Thus, the fixation target position for photographing the peripheral portion of the fundus is changed to the fixation target position for photographing the central portion of the fundus in synchronization with the switching from the manual photographing mode to the automatic photographing mode by the switch 94a, thereby saving the trouble of switch operation.

Incidentally, in the above description, the switch 94a intended only for the purpose is used for switching between the automatic photographing mode and the manual photographing mode; however, if another switch doubles as the switch 94a, a configuration of the switches can be simplified. For example, the photographing starting switch 9 may double as the switch 94a. Specifically, when the switch 9 is pushed for 2 seconds or more, the control unit 100 takes a signal from the switch 9 as a signal of switching between the automatic photographing mode and the manual photographing mode. In this case, to avoid accidental photographing, a period when the switching is possible is set to a period when the monitor 8 is not displaying the observation image of the fundus, i.e., a period when the monitor 8 is displaying the observation image of the anterior-segment of the eye or the photographing image of the fundus. Since the monitor 8 displays the observation image of the fundus at the time of fundus photographing, if the monitor 8 is displaying the observation image of the fundus and the switch 9 is pushed for less than 2 seconds, the control unit 100 regards the signal from the switch 9 as a trigger signal for starting photographing.

Figure 8:
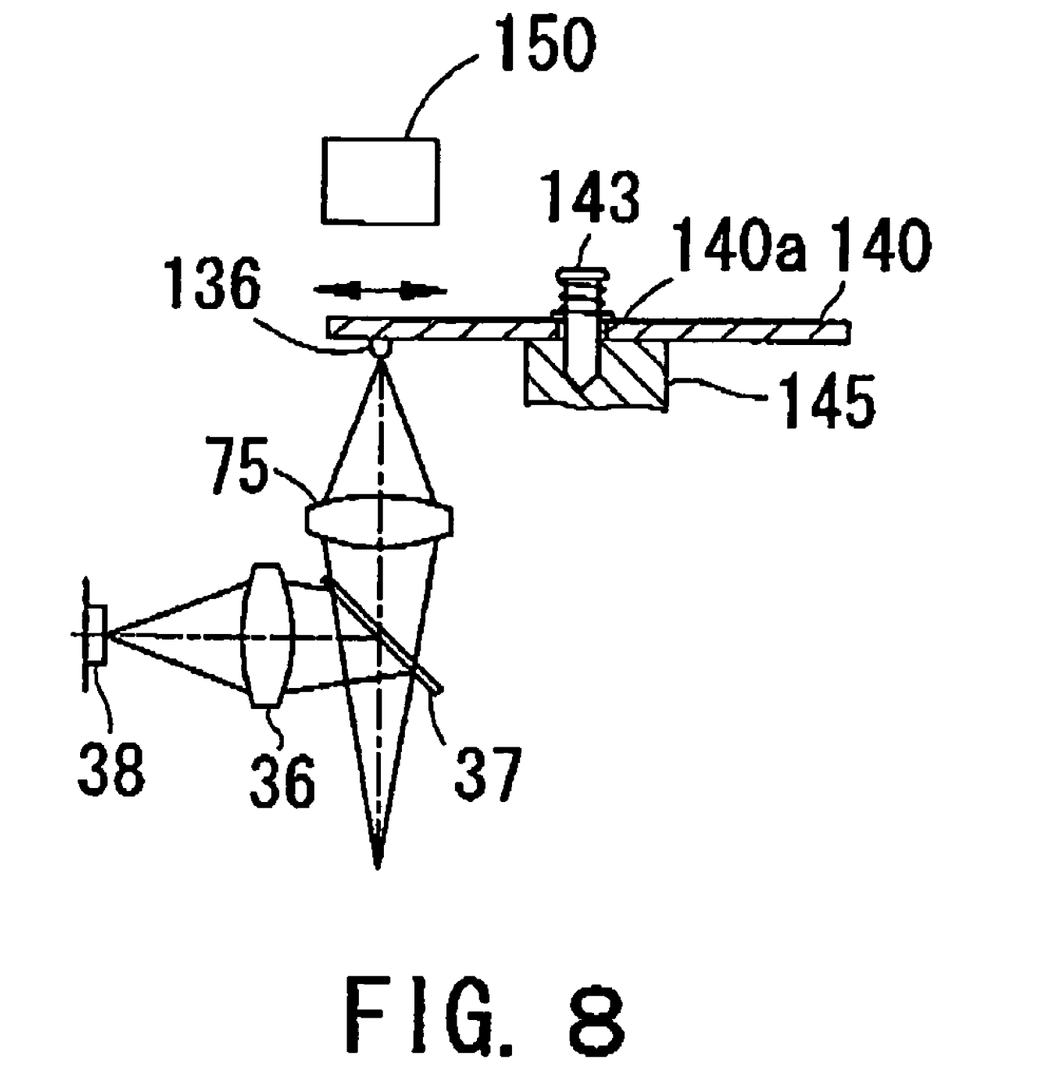
FIG. 8 is a view for illustrating a configuration in which the fixation target position is changed by manual operation by an examiner.

Additionally, a part of the fixation target presenting optical system 70 may be configured in such a manner that the presenting position of the fixation target is changed by manual operation as shown in FIG. 8. A point light source 136 being the fixation target is made movable within a plane approximately conjugate with the fundus Ef through operation of a lever 140. A slot 140a is formed in the lever 140 on which the point light source 136 is mounted, and the lever 140 is held so as to slide freely on a housing part 145 of the fundus camera by means of a screw 143 or the like. A sensor 150, which detects whether or not the point light source 136 is in the presenting position for photographing the central portion of the fundus, detects the position of the point light source 136 deviating from the position for photographing the central portion of the fundus when the lever 140 is moved in order to photograph the peripheral portion of the fundus. Hence, based on a detection signal therefrom, the control unit 100 may control to switch from the automatic photographing mode to the manual photographing mode.

The foregoing description of the preferred embodiments of the invention has been presented for purposes of illustration and description. It is not intended to be exhaustive or to limit the invention to the precise form disclosed, and modifications and variations are possible in the light of the above teachings or may be acquired from practice of the invention. The embodiments chosen and described in order to explain the principles of the invention and its practical application to enable one skilled in the art to utilize the invention in various embodiments and with various modifications as are suited to the particular use contemplated. It is intended that the scope of the invention be defined by the claims appended hereto, and their equivalents.

What is claimed is:

1. A fundus camera for photographing a fundus of an eye to be examined, the fundus camera comprising:
   a photographing optical system having a photographing optical axis, a focusing lens movable in a direction of the photographing optical axis, and an image-pickup element;
   alignment-state detection means for detecting a state of alignment of the photographing optical system with the eye;
   focusing-state detection means for detecting a state of focusing of the photographing optical system on the fundus;
   a fixation target Presenting unit which presents a fixation target for guiding a visual line to the eye, in which a presenting position of the fixation target is changeable between a reference position which is a position for photographing a central portion of the fundus and a peripheral position which is a position for photographing a peripheral portion of the fundus;
   a photographing starting switch;
   photographing-mode switching means for switching between a manual photographing mode in which photographing is performed based on an operation signal from the photographing starting switch, and an automatic photographing mode in which photographing is automatically performed based on results detected by the alignment-state detection means and the focusing-state detection means;
   fixation target presentation control means for controlling the fixation target presenting unit so that the Presenting position of the fixation target is brought to the reference position at a time of switching from the manual photographing mode to the automatic photographing mode, even though the presenting position of the fixation target is set to the peripheral position; and
   presenting-position changing means for inputting a change signal for changing the presenting position of the fixation target,
   wherein the photographing-mode switching means switches from the automatic photographing mode to the manual photographing mode based on a change signal for changing the presenting position of the fixation target from the reference position to the peripheral position.

2. The fundus camera according to claim 1, wherein the presenting-position changing means inputs one of an instruction signal and a detection signal as to a change of the presenting position of the fixation target.

3. The fundus camera according to claim 1, further comprising:
   an optical system moving unit which relatively moves the photographing optical system with respect to the eye;
   alignment means for detecting an alignment target projected onto the eye and controlling the optical system moving unit based on a result of a detection of the alignment target;
   a lens moving unit which moves a focusing lens in the direction of the photographing optical axis; and
   focusing means for detecting a focus target projected onto the fundus and controlling the lens moving unit based on a result of a detection of the focus target.

4. A fundus camera for photographing a fundus of an eye to be examined, the fundus camera comprising:
   a photographing optical system having a photographing optical axis, a focusing lens movable in a direction of the photographing optical axis, and an image-pickup element;
   alignment-state detection means for detecting a state of alignment of the photographing optical system with the eye;
   focusing-state detection means for detecting a state of focusing of the photographing optical system on the fundus;
   a fixation target presenting unit which presents a fixation target for guiding a visual line to the eye, in which a presenting position of the fixation target is changeable between a reference position which is a position for photographing a central portion of the fundus and a peripheral position which is a position for photographing a peripheral portion of the fundus;
   a photographing starting switch;
   photographing-mode switching means for switching between a manual photographing mode in which photographing is performed based on an operation signal from the photographing starting switch, and an automatic photographing mode in which photographing is automatically performed based on results detected by the alignment-state detection means and the focusing-state detection means; and
   presenting-position changing means for inputting a change signal for changing the presenting position of the fixation target,
   wherein the photographing-mode switching means switches from the automatic photographing mode to the manual photographing mode based on a change signal for changing the presenting position of the fixation target from the reference position to the peripheral position.

5. The fundus camera according to claim 4, wherein the presenting-position changing means inputs one of an instruction signal and a detection signal as to a change of the presenting position of the fixation target.

6. The fundus camera according to claim 4, further comprising:
   an optical system moving unit which relatively moves the photographing optical system with respect to the eye;
   alignment means for detecting an alignment target projected onto the eye and controlling the optical system moving unit based on a result of a detection of the alignment target;
   a lens moving unit which moves the focusing lens in the direction of the photographing optical axis; and
   focusing means for detecting a focus target projected onto the fundus and controlling the lens moving unit based on a result of a detection of the focus target.

7. A fundus camera for photographing a fundus of an eye to be examined, the fundus camera comprising:
   a photographing optical system having a photographing optical axis, a focusing lens movable in a direction of the photographing optical axis, and an image-pickup element;
   an optical system moving unit which relatively moves the photographing optical system with respect to the eye;
   automatic alignment means for detecting an alignment target projected onto the eye and controlling the optical system moving unit based on a result of a detection of the alignment target;
   a lens moving unit which moves the focusing lens in the direction of the photographing optical axis;
   automatic focusing means for detecting a focus target projected onto the fundus and controlling the lens moving unit based on a result of a detection of the focus target;
   a fixation target presenting unit which presents a fixation target for guiding a visual line to the eye, in which a presenting position of the fixation target is changeable between a reference position which is a position for photographing a central portion of the fundus and a peripheral position which is a position for photographing a peripheral portion of the fundus;
   photographing-mode switching means for switching between an automatic photographing mode in which the automatic alignment means and the automatic focusing means are actuated, and a manual photographing mode in which actuation of the automatic alignment means and the automatic focusing means is stopped; and
   presenting-position changing means for inputting a changing signal for changing the presenting position of the fixation target;
   wherein the photographing-mode switching means switches from the automatic photographing mode to the manual photographing mode based on a changing signal for changing the presenting position of the fixation target from the reference position to the peripheral position.

8. The fundus camera according to claim 7, wherein the presenting-position changing means inputs one of an instruction signal and a detection signal as to a change of the presenting position of the fixation target.

* * * * *